US006861441B1

(12) United States Patent
Clayton et al.

(10) Patent No.: US 6,861,441 B1
(45) Date of Patent: Mar. 1, 2005

(54) USE OF EP4 RECEPTOR LIGANDS IN THE TREATMENT OF NEUROPATHIC PAIN AND COLON CANCER

(75) Inventors: Nicholas Maughan Clayton, Stevenage (GB); Susanne Denise Collins, Stevenage (GB); Steven Michael Foord, Stevenage (GB); Gerard Martin Paul Giblin, Welwyn (GB); Richard John Coles, Uxbridge (GB); Mark Bamford, Harlow (GB); Richard Green, deceased, late of Portland, ME (US); by Jennifer M Doughty, legal representative, Portland, ME (US)

(73) Assignee: SmithKline Beecham Corporation, Philadelphia, PA (US)

( * ) Notice: Subject to any disclaimer, the term of this patent is extended or adjusted under 35 U.S.C. 154(b) by 133 days.

(21) Appl. No.: 10/049,142

(22) PCT Filed: Aug. 8, 2000

(86) PCT No.: PCT/EP00/07669

§ 371 (c)(1),
(2), (4) Date: Feb. 5, 2002

(87) PCT Pub. No.: WO01/10426

PCT Pub. Date: Feb. 15, 2001

(30) Foreign Application Priority Data

Aug. 10, 1999 (GB) .............................................. 9918745
Dec. 1, 1999 (GB) .............................................. 9928437

(51) Int. Cl.$^7$ ....................... A61K 31/40; C07D 209/56
(52) U.S. Cl. ...................... 514/411; 514/408; 514/410; 514/411; 514/359; 548/400; 548/416; 548/430; 548/435
(58) Field of Search ........................................ 514/411

(56) References Cited

U.S. PATENT DOCUMENTS

| | | | |
|---|---|---|---|
| 4,327,092 A | 4/1982 | Collington et al. | |
| 5,834,463 A | 11/1998 | Ohkawa et al. | |

FOREIGN PATENT DOCUMENTS

| | | |
|---|---|---|
| EP | 0 501 579 | 9/1992 |
| EP | 0 520 573 A | 12/1992 |
| GB | 2 330 307 A | 4/1999 |
| GB | 23302307 | * 4/1999 |

OTHER PUBLICATIONS

Katzung, Basic and Clinical Pharmacology, 1995, p. 536–537.*
Takakazu, Oka., et al. "Biphasic modulation in the trigeminal nociceptive neuronal responses by the intracerebroventricular prostaglandin E2 may be mediated through different ep receptors subtypes in rates." Elsevier Science Brain Research 771 (1997) pp. 278–284.

Fedyk, Eric R., et al. "A molecular analysis of PGE receptor (EP) expression on normal and transformed B Lymphocytes: comexpression of $EP_1$, $EP_2$, $EP_{3\beta}$ and $EP_4$." Molecular Immunology vol. 33, No. 1 pp. 33–45 1996 Elsevier Science.

Zeng, Li, et al. "Selective Regulation of RNK–16 cell Matrix Metalloproteinases by the $Ep_4$ subtype of prostaglandin $E_2$ receptor." American Chemical Society, Biochemistry 1996 vol 35 pp. 7159–7164.

Coleman, R.A., et al. "A Novel inhibitory prostanoid receptor in piglet saphenous vein." Butterworth–Heinemann—Prostaglandins 1994 vol 47 pp. 151–168.

Mori, K., et al. "Gene Expression of the human prostaglandin E receptor $EP_4$ subtype: differential regulation in monocytoid and lymphoid lineage cells by phorbol ester." J. Mol Med 1996, vol. 74 pp. 333–336.

Ono, K., et al "Important role of $EP_4$ a subtype of prostaglandin (PG) E receptor, in osteoclast–like cell formation from mouse bone marrow cells induced by $PGE_2$ " Jm of Endocrinology 1998, 158., pp. R1–R5.

Fedyk, R., Eric., et al "Prostaglandin $E_2$ receptors of the $EP_2$ and $EP_4$ subtypes regulate activation and differentiation of mouse B lymphocytes to IgE–secreting cells." Proc Natl acad Sci USA vol. 93 pp. 10978–10983 Oct. 1996 Immunology.

Arakawa, T., et al., "Prostanoid receptors of Murine NIH 3T3 and RAW 264.7 Cells." The American Soc of Biochemistry & Molecular biology Inc vol. 271 No. 47 Issue Nov. 22, 1996, pp. 29569–29575.

Mori, K., et al. "Gene expression of the human prostaglandin E receptor $EP_4$ subtype: differential regulation in monocytoid and lymphoid lineage cells by phorbol ester." J. Mol Med 1996 74: pp. 333–336.

Sato, T., et al. "Prostaglandin $E_2$ mediates parathyroid hormone induced osteoclast formation by cyclic AMP indepnedent Mechanism." Eicosanoids and other Bioactive Lipids in cancer inflammation & Radiation Injury 3, edited by Honn et al Plenum Press New York 1997 pp. 383–386 No. 57.

Minami, T., et al., "Characterization of EP–receptor subtypes involved in allodynia & heperalgesia induced by intrathecal administration of prostaglandin $E_2$ to mice." Br J Pharmacol (1994) 112, pp. 735–740.

Minami, T. et al. "Blockade by ONO–NT–012 a unique prostanoid analogue of prostaglandin $E_2$–induced allodynia in conscious mice." Br. Jml of Pharmacology 1995 115, pp. 73–76.

(List continued on next page.)

*Primary Examiner*—Russell Travers
(74) *Attorney, Agent, or Firm*—Lorie Ann Morgan

(57) ABSTRACT

The present invention relates to the use of an EP4 receptor ligand in the manufacture of a medicament for use in the treatment of neuropathic pain, colon cancer, migraine, and for increasing the latency of HIV infection.

8 Claims, No Drawings

OTHER PUBLICATIONS

Nishigaki, N. et al. "Two $G_s$–Coupled prostaglandin E receptor subytpes, EP2 and EP4 differ in desenitization and sensitivity to the metabolic inactivation of the agonist." The Amer Soc for Pharma & Exper Thera. Molecular Pharmacology 50: pp. 1031–1037 (1996).

Marshall, F., et al. "Characterization of [H]–Prostaglandin $E_2$ Bind to Prostaglandin $EP_4$ Receptors Expressed with Semliki Forest Virus." Bristish Journal of Pharmacology, 121:1673–1678 (1997).

Coleman, R., et al. "$EP_4$–Receptors and Cyclic AMP in Pig Venous Smooth Muscle: Evidence with Agonists and the $EP_4$–Antagonist, AH22921." Advances in Prostaglandin, Thromboxane, and Luekotriene Research. 23:241–246 (1995).

* cited by examiner

USE OF EP4 RECEPTOR LIGANDS IN THE TREATMENT OF NEUROPATHIC PAIN AND COLON CANCER

CROSS-REFERENCES TO RELATED APPLICATIONS

This application is a Rule 371 Application of PCT Application No. EP00/07669, filed 8 August 2000, which claims priority to GB Application Serial No. 9918745.2, filed 10 Aug. 1999 and GB Application Serial No. 9928437.4, filed 1 Dec. 1999.

BACKGROUND OF THE INVENTION

The present invention relates to new uses for EP4 receptor ligands.

The EP4 receptor is a 7-transmembrane receptor and its natural ligand is the prostaglandin $PGE_2$. $PGE_2$ also has affinity for the other EP receptors (types EP1, EP2 and EP3).

Compounds exhibiting EP4 binding activity have been described in, for example, WO00/18744, WO00103980, WO00/15608, WO01/16760, WO00/21532, WO98/55468, EP0855389 and EP0985663. GB2330307 describes the use of EP4 antagonists in the treatment of conditions with accelerated bone resorption.

BRIEF SUMMARY OF THE INVENTION

It has now been found that EP4 receptor ligands are of use in the treatment of A neuropathic pain, colon cancer, migraine and in increasing the latency of HIV infection.

It is believed that selective EP4 receptor ligands exhibit a number of advantages over current non-steroidal anti-inflammatory (NSAID) and cyclo-oxygenase-2 inhibitor (COX-2i) drugs which act via a number of prostaglandin pathways. By selectively binding to the EP4 receptor, the beneficial activities of other prostaglandin pathways are retained. The use according to the instant invention therefore provides greater efficacy and improved gastro-intestinal safety over NSAIDs.

The present invention provides the novel use of an EP4 receptor ligand in the manufacture of a medicament for use in the treatment of neuropathic pain, colon cancer, migraine and for increasing the latency of HIV infection.

In a further aspect the invention provides a novel method of increasing the latency of HIV infection; and for treating migraine, neuropathic pain, and colon cancer; in a mammal, including man, comprising administration of an effective amount of an EP4 receptor ligand.

In a further aspect the present invention provides the novel use of an EP4 receptor antagonist in the manufacture of a medicament for use in the treatment of neuropathic pain, colon cancer, migraine and for increasing the latency of HIV infection.

In a further aspect the invention provides a novel method of increasing the latency of HIV infection; and for treating migraine, neuropathic pain, and colon cancer; in a mammal, including man, comprising administration of an effective amount of an EP4 receptor antagonist.

It is to be understood that reference to treatment as used herein includes treatment of established symptoms and prophylactic treatment, unless explicitly stated otherwise.

Suitable EP4 receptor ligands for use in the present invention include those described in GB2330307, WO00/18744, WO00/03980, WO00/15608, WO00/16760, WO00/21532, WO98/55468, EP0855389 and EP0985663, all incorporated by reference herein. A preferred EP4 receptor ligand for use in the present invention is the compound [4-(4,9-diethoxy-1-oxo-1,3-dihydro-2H-benzo[f]isoindol-2-yl)phenyl]acetic acid and pharmaceutically acceptable derivatives thereof of formula (IF) below.

Compounds described in GB2330307 are [1α(Z),2β,5α]-(±)-7-[5-[[(1,1'-biphenyl)-4-yl]methoxy]-2-(4-morpholinyl)-3-oxocyclopentyl]4-heptenoic acid and the physiologically acceptable salts and solvates thereof and [1R[1α(Z),2β,5α]]-(−)-7-[5-[[1,1'-biphenyl)-4-yl]methoxy]-2-(4-morpholinyl)-3-oxocyclopentyl]4-heptenoic acid and the physiologically acceptable salts and solvates thereof.

[1α(Z),2β,5α]-(±)-7-[5-[[(1,1'-Biphenyl)-4-yl]methoxy]-2-(4-morpholinyl)-3 oxocyclopentyl]4-heptenoic acid and the physiologically acceptable salts and solvates thereof and [1R[1α(Z),2β,5α]]-(−)-7-[5-[1,1'-biphenyl)-4-yl]methoxy] 2-(4-morpholinyl)-3-oxocyclopentyl]4-heptenoic acid and the physiologically acceptable salts and solvates thereof may be prepared and formulated according to the methods described in UK Patent Application No GB 2075503.

Compounds described in WO00/18744 are oxazole compounds of formula (I)

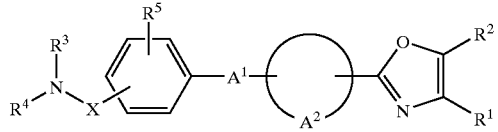

(I)

wherein
$R^1$ is aryl which may be substituted with halogen(s),
$R^2$ is aryl which may be substituted with halogen(s),
X is single bond, C=O or $SO_2$,
$R^3$ and $R^4$ are independently hydrogen or suitable substituent,
(wherein X is C=O, neither $R^3$ nor $R^4$ is hydrogen),
$R^3$ and $R^4$ may be linked together to form

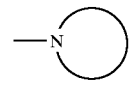

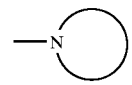

is N-containing heterocyclic group which may be substituted with one or more suitable substituent(s),
$R^5$ is
(1) hydrogen,
(2) hydroxy,
(3) carboxy, or
(4) protected carboxy,
$A^1$ is lower alkylene or single bond,

is cyclo ($C_{3-C9}$) alkane or cyclo ($C_5$–$C_9$)alkene,
or a pro-drug thereof, or a pharmaceuticially acceptable salt thereof, which may be prepared according to the method described therein.

Compounds described in WO00/03980 are 5-thia-ω-substituted phenyl-prostaglandin E derivatives of formula (IA)

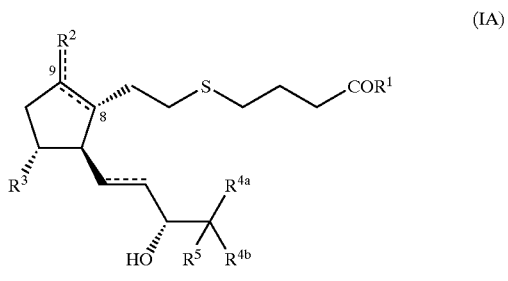

wherein each symbol is as defined in the specification.

Compounds described in WO00/1560B are ω-substituted phenyl-prostaglandin E derivatives of formula (IB)

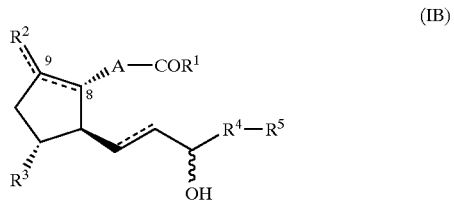

wherein each symbol is as defined in the specification.

Compounds described in WO00/21532 are
5-butyl-2,4-dihydro-4-[[2'-[N-(3-chloro-2-thiophenecarbonyl)sulfamoyl]biphenyl-4-yl]methyl]-2{2-(trifluoromethyl)phenyl]-1,2,4-triazol-3-one potassium salt,
5-butyl-2,4-dihydro-4-[[2'-[N-(2-methyl-3-furoyl)sulfamoyl]biphenyl4-yl]methyl]2-[2-(trifluoromethyl)phenyl]-1,2,4-triazol-3-one,
5-butyl-2,4-dihydro-4[[2'-[N-(3-methyl-2-thiophenecarbonyl)sulfamoyl]biphenyl-4-yl]methyl]-2-[2-(trifluoromethyl)phenyl]-1,2,4-triazol-3-one,
5-butyl-2,4-dihydro-4-[[2'-[N-(2-thiophenecarbonyl)sulfamoyl]biphenyl4-yl]methyl]-2-[(2-(trifluoromethyl)phenyl]-1,2,4-triazol-3-one,
5-butyl-2,4-dihydro-4-[[2'-[N-[2-(methylpyrrole)carbonyl]sulfamoyl]biphenyl-4-yl]methyl]2-[(2-(trifluoromethyl)phenyl]-1,2,4-triazol-3-one,
and the pharmaceutically acceptable salts thereof, and mixtures thereof.

Compounds described in WO98/55468 are azole compounds of formula (IC):

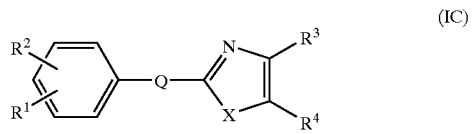

wherein $R^1$ is lower alkyl substituted with hydroxy, protected carboxy or carboxy; carboxy; protected carboxy; carbamoyl; a heterocyclic group; cyano; hydroxy; halo (lower)alkylsulfonyloxy; lower alkoxy optionally substituted with hydroxy or carbamoyl; aryl substituted with carboxy, protected carboxy, carbamoyl or a heterocyclic group; or amino optionally substituted with protected carboxy or lower alkylsulfonyl, $R^2$ is hydrogen or lower alkyl,
$R^3$ is aryl optionally substituted with halogen,
$R^4$ is aryl optionally substituted with halogen,
Q is

[in which -$A^1$- is a single bond or lower alkylene,

is cyclo ($C_5$–$C_9$)alkene, cyclo ($C_3$–$C_9$)alkane, bicyclo ($C_6C_9$)alkene or bicyclo ($C_5$–$C_9$)alkane, and -$A^3$- is a single bond or lower alkylene], and X is O, NH or S; which may be prepared according to the methods described therein.

Compounds described in EP0855389 are 3,7-dithiaprostanoic acid derivatves of the formula (ID):

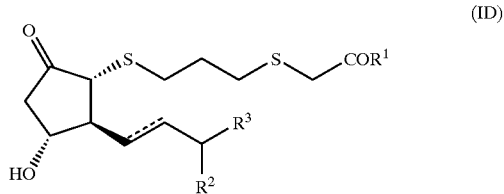

(wherein $R^1$ is hydroxy, C1–4 alkoxy or a group of the formula:

—$NR^6R^7$ wherein $R^6$ and $R^7$, independently, are hydrogen atom or C1–4 alkyl, $R^2$ is hydrogen atom or hydroxy,
$R^3$ is
(i) C1–8 alkyl, C2–8 alkenyl or C2–8 alkynyl,
(ii) phenyl or C3–7 cycloalkyl,
(iii) C1–8 alkyl, C2–8 alkenyl or C2–8 alkynyl substituted by phenyl or C3–7 cycloalkyl, with the provisio that alkyl, alkenyl, alkynyl in (i) or (iii) may be substituted by one hydroxy group, when $R^2$ is hydrogen atom;

the symbol  is a double or single bond;
the formula including the 8-epi equilibrium compound thereof);
a non-toxic salt thereof or a cyclodextrin clathrate thereof, which may be prepared according to the methods described therein.

Compounds described in EP0985663 are 3,7-dithiaprostanoic acid derivatives of the formula (1 E)

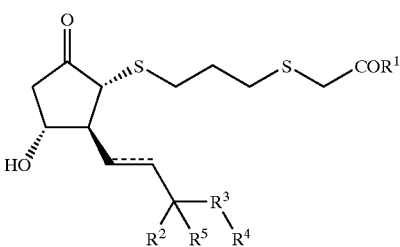

(1E)

wherein R¹ is hydroxy, C1–6 alkyloxy or a group of the formula:

NR⁶R⁷

(in which R⁶ and R⁷ are independently hydrogen or C1–6 alkyl);
R² is hydrogen or hydroxy;
R³ is single bond or C1–6 alkylene;
R⁴ is
(i) C1–8 alkyl, C2–8 alkenyl or C2–8 alkynyl substituted by 1 to 3 substituents selected from $C_{1-6}$ alkyloxy and halogen atom(s),
(ii) phenyloxy or C3–7 cycloalkyloxy,
(iii) furyl, furyloxy, thienyl, thienyloxy, naphthyl, naphthyloxy, phthalanyl or phthalanyloxy,
(iv) phenyl, phenyloxy, C3–7 cycloalkyl or C3–7 cycloalkyloxy substituted by 1 to 3 substituents selected from the following groups:
C1–6 alkyl, C2–6 alkenyl, C2–6 alkynyl, C1–6 alkyloxy, C1–6 alkyloxy-C1–6 alkyl, C1–6 alkyloxy-C1–6 alkyloxy, C2–6 alkenyloxy-C1–6 alkyl, C1–6 alkyl substituted by 1 to 3 of hydroxy, C1–6 alkyl substituted by 1 to 3 of halogen atom(s), C1–6 alkylthio, C1–6 alkylthio-C1–6 alkyl, C1–6 alkylthio-C1–6 alkyloxy, C2–6 alkenylthio-C1–6 alkyl, C1–6 alkylsulfonyl, halogen, trihalomethyl, cyano, nitro, amino, hydroxy, C3–7 cycloalkyl, C3–7 cycloalkyloxy, C3–7 cycloalky-C1–6 alkyl, C3–7 cycloalkyloxy-C1–6 alkyl, phenyl, phenyloxy, phenyl-C1–6 alkyl, phenyl-C2–6 alkenyl, phenyl-$C_2$–6 alkynyl, phenyloxy-C1–6 alkyl, phenyloxy-C2–6 alkenyl, phenyloxy-C2–6 alkynyl, furyl, furyloxy, furyl-C1–6 alkyl, furyloxy-C1–6 alkyl, thienyl, thienyloxy, thienyl-C1–6 alkyl and thienyloxy-C1–6 alkyl (the above mentioned phenyl, furyl, thienyl and cycloalkyl being optionally substituted by 1 to 3 substituents selected from C1–6 alkyl, C1–6 alkyloxy, C1–6 alkyloxy-C1–6 alkyl, nitro, halogen, trihalomethyl, amino and hydroxy), or
(v) furyl, furyloxy, thienyl, thienyloxy, naphthy, naphthyloxy, phthalanyl or phthalanyloxy substituted by 1 to 3 substituents selected from the following groups:
C1–6 alkyl, C2–6 alkenyl, C2–6 alkynyl, C1–6 alkyloxy, C1–6 alkyloxy-C1–6 alkyl, C1–6 alkyloxy-C1–6 alkyloxy, C2–6 alkenyloxy-C1–6 alkyl, C1–6 alkyl substituted by 1 to 3 of hydroxy, C1–6 alkyl substituted by 1 to 3 of halogen atom(s), C1–6 alkylthio, C1–6 alkylthio-C1–6 alkyl, C1–6 alkylthio-C1–6 alkyloxy, C2–6 alkenylthio-C1–6 alkyl, C1–6 alkylsulfonyl, halogen, trihalomethyl, cyano, nitro, amino, hydroxy, C3–7 cycloalkyl, C3–7 cycloalkyloxy, C3–7 cycloalkyl-C1–6 alkyl, C3–7 cycloalkyloxy-C1–6 alkyl, phenyl, phenyloxy, phenyl-C1–6 alkyl, phenyl-C2–6 alkenyl, phenyl-C2–6 alkynyl, phenyloxy-C1–6 alkyl, phenyloxy-C2–6 alkenyl, phenyloxy-C2–6 alkynyl, furyl, furyloxy, furyl-C1–6 alkyl, furyloxy-C1–6 alkyl, thienyl, thienyloxy, thienyl-C1–6 alkyl and thienyloxy-CIS alkyl (the above mentioned phenyl, furyl, thienyl and cycloalkyl being optionally substituted by 1 to 3 substituents selected from CIS alkyl, C1–6 alkyloxy, C1–6 alkyloxy-C1–6 alkyl, nitro, halogen, trihalomethyl, amino and hydroxy);
R⁵ is hydrogen or C1 alkyl;
and the symbol ____ is double bond or single bond;
the formula including the 8-epi equilibrium compound; with the proviso that when R² is hydrogen, C1–6 alkylene represented by R³ may be substituted by a hydroxy group;
or a non-toxic salt thereof or cyclodextrin clathrate thereof, which may be prepared according to the methods described therein.

As mentioned above, a preferred EP4 receptor ligand for use in the present invention is the compound [4(4,9-diethoxy-1-oxo-1,3-dihydro-2H-benzo[f]isoindol-2-yl)phenyl]acetic acid of formula (IF) below.

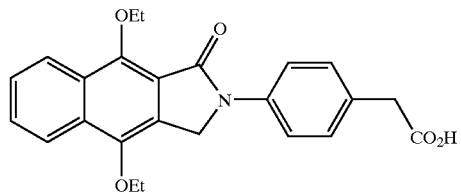

(IF)

The compound of formula (IF) and pharmaceutically acceptable derivatives thereof is novel and therefore forms a further feature of the invention.

The ability of the compounds to bind to EP4 receptors may be demonstrated in the Human $EP_4$ Scintillation Proximity Assay.

Quantification of radioligand binding by scintillation proximity assay (SPA) is a long-established principle. Briefly, the affinity of compounds for a receptor is assessed by the specific competition between known quantities of radiolabelled ligand and compound for that receptor. Increasing concentrations of compound reduce the amount of radiolabel that binds to the receptor. This gives rise to a diminishing scintillation signal from SPA beads coated with membranes that bear the receptor. The signal may be detected with a suitable scintillation counter and the data generated may be analysed with suitable curve-fitting software.

The human $EP_4$ SPA assay (hereafter referred to as 'the assay') utilises membranes prepared from Chinese Hamster Ovary (CHO cells) infected with Semliki Forest Virus (SFV). The virus is previously transfected with an SFV-1 RNA construct containing the $hEP_4$ receptor. Cells washed free of media are homogenised in a pH-buffered medium containing peptidase inhibitors. A suitable buffer is of the following composition: 50 mM HEPES, 1 mM EDTA, 25 µg/ml bacitracin, 100 µM leupeptin, 1 mM PMSF, 2 µM Pepstatin A, pH adjusted to 7.4 with KOH. Following removal of cell debris by a low-speed centrifugation, a pellet of membranes is prepared by a high-speed (48000 g) centrifugation of the resulting supernatant. Membrane suspensions such as that described may be stored at −80° C. until used.

For assay, membranes expressing human EP4 receptors are diluted in a pH-buffered medium and mixed with SPA beads coated with a suitable substance to facilitate the adhesion of membranes to the beads. The concentrations of membrane protein and SPA beads chosen should result in SPA binding signal of at least 300 corrected counts per minute (CCPM) when tritiated radioligand at a concentration close to its $K_d$ (affinity value) is combined with the mixture. Nonspecific binding (nsb) may be determined by competition between the radiolabelled ligand and a saturating concentration of unlabelled ligand. In order to quantify the affinity of EP4 receptor ligands, compounds are diluted in a stepwise manner across the wells of a 96-well plate. Radioligand, compound, and unlabelled ligand are then added to a 96-well plate suitable for the measurement of SPA binding signals prior to the addition of bead/membrane mixture to initiate the binding reaction. Equilibrium may be achieved by incubation at room temperature for 120 minutes prior to scintillation counting. The data so generated may be analysed by means of a computerised curve-fitting routine in order to quantify the concentration of compound that displaces 50% of the specific radioligand binding ($IC_{50}$). The affinity ($pK_i$) of the compound may be calculated from the $IC_{50}$ by application of the Cheng-Prusoff correction. Suitable reagents and protocols are: reaction buffer containing 50 mM HEPES, 10 mM $MgCl_2$, pH adjusted to 7.4 with KOH; SPA beads coated with wheatgerm agglutinin; 1.25 nM [$^3$H]-prostaglandin $E_2$ as radioligand; 10 $\mu$M prostaglandin $E_2$ as unlabelled ligand; a three-fold dilution series of compound starting at 10 $\mu$M and ending at 0.3 nM is adequate.

By application of this technique, 4-(4,9-diethoxy-1-oxo-1,3-dihydro-2H-benzo[f]isoindol-2-yl)phenyl]acetic acid (IF) had a pKi of 7.00±0.28 (mean±standard deviation of the mean; n=87).

The novel use of EP4 receptor ligands in the treatment of neuropathic pain has been demonstrated in the following test.

The chronic constriction injury (CCI) model was used to induce the neuropathic hypersensitivity (Bennett & Xie, 1988) in male random hooded rats.

Under isoflurane anaesthesia, the common left sciatic nerve was exposed at mid thigh level and four loose ligatures of Chromic gut tied around it. The wound was then closed and secured using suture clips. The surgical procedure was identical for the sham operated animals except the sciatic nerve was not ligated. The rats were allowed a period of seven days to recover from the surgery before behavioural testing began.

4-(4,9-diethoxy-1-oxo-1,3-dihydro-2H-benzo[f]isoindol-2-yl)phenyl]acetic acid (IF) (10 mgkg-1 b.i.d. PO) was dosed chronically for 14 days (days 20–33 postoperative). A reversal of the CCI-induced decrease in paw withdrawal threshold became apparent following 3 days of chronic dosing which was maximal after 1 week. This reversal was maintained throughout the remainder of the dosing period. Following cessation of the drug treatment the paw withdrawal threshold returned to that of the vehicle treated CCI-operated animals.

The compounds for use in the invention may be administered orally at a dose of from 0.1 to 10 mg/kg body weight per day and more particularly 0.3 to 3 mg/kg body weight per day, calculated as the free base. The dose range for adult human beings is generally from 8 to 1000 mg/day, such as from 35 to 800 mg/day, preferably 20 to 200 mg/day, calculated as the free base.

The precise amount of the compounds administered to a host, particularly a human patient, will be the responsibility of the attendant physician. However, the dose employed will depend upon a number of factors including the age and sex of the patient, the precise condition being treated and its severity, and the route of administration.

The compounds and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible for the compounds to be administered as the raw chemical, it is preferable to present it as a pharmaceutical formulation. The formulations comprise the compounds together with one or more acceptable carriers or diluents therefor and optionally other therapeutic ingredients. The carrier(s) must be "acceptable" in the sense of being compatible with the other ingredients of the formulation and not deleterious to the recipient thereof.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may al so be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

The EP4 receptor ligand for use in the instant invention may be used in combination with other therapeutic agents, for example COX-2 inhibitors, such as celecoxib, rofecoxib, valdecoxib or parecoxib; 5-lipoxygenase inhibitors; low dose aspirin; NSAID's, such as diclofenac, indomethacin or ibuprofen; leukotriene receptor antagonists; DMARD's such as methotrexate; adenosine 1 agonists; recombinant human TNF receptor fusion proteins such as etanercept; sodium channel antagonists, such as lamotrigene; NMDA antagonists, such as glycine antagonists; and 5HT₁ agonists, such as triptans, for example sumatriptan, naratriptan, zolmitriptan, eletriptan, frovatriptan, almotriptan or rizatriptan. When the compounds are used in combination with other therapeutic agents, the compounds may be administered either sequentially or simultaneously by any convenient route.

The invention thus provides, in a further aspect, the use of a combination comprising an EP4 receptor ligand with a further therapeutic agent in the treatment of migraine, neuropathic pain, colon cancer and in increasing the latency of HIV infection.

In a further aspect, the invention provides the use of a combination comprising an EP4 receptor antagonist with a further therapeutic agent in the treatment of migraine, neuropathic pain, colon cancer and in increasing the latency of HIV infection.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When an EP4 receptor ligand is used in combination with a second therapeutic agent active against the same disease, the dose of each compound may differ from that when the compound is used alone. Appropriate doses will be readily appreciated by those skilled in the art.

Likewise, when an EP4 receptor antagonist is used in combination with a second therapeutic agent active against the same disease, the dose of each compound may differ from that when the compound is used alone. Appropriate doses will be readily appreciated by those skilled in the art.

Preferred unit dosage formulations are those containing an effective daily dose, as herein above recited, or an appropriate fraction thereof, of the active ingredient. Conveniently that may be from 5 mg to 1000 mg, such as from 8 mg to 1000 mg, more conveniently 35 mg to 800 mg, and most conveniently 20 to 200 mg, calculated as the free base.

The compound of formula (IF) and pharmaceutically acceptable derivatives thereof may be prepared by any method known in the art for the preparation of compounds of analogous structure.

A suitable method for the preparation of compound (IF) and pharmaceutically acceptable derivatives thereof is described below and forms a further aspect of the invention.

Compound (IF) may be prepared by reducing the compound

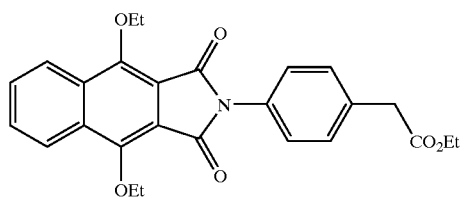

with a suitable reducing agent, for example zinc in acetic acid at elevated temperature, followed by separation of isomers and deprotection (eg. with aqueous base at elevated temperature).

The following Example which should not be construed as constituting a limitation thereto is provided to illustrate the invention.

¹H NMR spectra were obtained at 400 MHz on a Bruker DPX400 spectrophotometer. J values are given in Hz. Mass spectra were obtained on a Micromass series II MS (electrospray positive or negative).

Intermediate 1

Ethyl 1,4-dihydroxy-2,3-naphthalenedicarboxylate

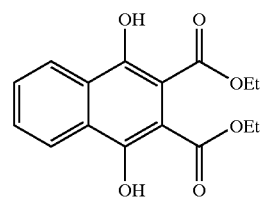

Sodium (60 g, 2.6 mol) was dissolved in ethanol (1.2 L) and the mixture was cooled to 40° C. Diethylphthalate (960 ml, 4.83 mol) was added and the mixture heated under nitrogen until the temperature reached 115° C. Diethyl succinate (211.39, 1.21 mol) was added dropwise over 45 min. The reaction was heated at 115° C. for a further 45 min, cooled to room temperature and poured onto water (1.2 L). Ethyl acetate (1 L) was added and stirred, the layers were separated and the organics were extracted with sodium hydroxide solution (2N, 1 L). The combined aqueous was acidified to pH 3 and the mixture extracted with ethyl acetate (2×1 L). The combined organics were washed with a saturated solution of sodium hydrogen carbonate (2×1.5 L), then brine, dried (MgSO₄), filtered and the solvent evaporated under vacuum. The residue was purified using a 2.5 kg Biotage column eluting with 5% ethyl acetate/hexane to give ethyl 1,4-dihydroxy-2,3-naphthalenedicarboxylate as a white solid, (60 g, 16%)

δH CDCl₃ 10.44, (2H, s), 8.34, (2H, m), 7.68, (2H, m), 4.37, (4H, q), 1.37, (6H, t).

Intermediate 2
Ethyl 1,4-diethoxy-2,3-naphthalenedicarboxylate

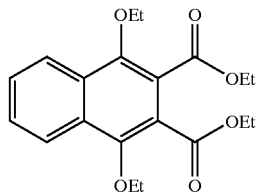

Ethyl 1,4-dihydroxy-2,3-naphthalenedicarboxylate (30 g, 98.6 mmol) and potassium carbonate (150 g, 1.09 mmol) were stirred in acetone (600 ml) under nitrogen. Iodoethane (150 g, 0.96 mol) was added and the mixture was stirred at reflux overnight. The reaction was cooled, diluted with ethyl acetate and filtered. The filtrate was evaporated to leave a brown oil, which was dissolved in toluene and washed with potassium hydroxide solution (5%, 150 ml) and brine. Drying over magnesium sulphate and evaporation of the solvent gave a yellow solid. Purification using an 800 g Biotage column gave ethyl 1,4-diethoxy-2,3-naphthalenedicarboxylate as a white solid (32 g, 90%).

$\delta$H CDCl$_3$ 8.16, (2H, m), 7.60, (2H, m), 4.40, (4H, q), 4.18, (4H, q), 1.50, (6H, t), 1.40, (6H, t).

Intermediate 3
1,4-Diethoxy-2,3-naphthalenedicarboxylic Acid

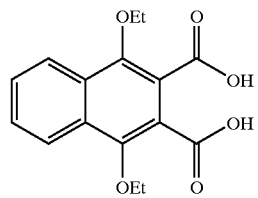

Ethyl 1,4-diethoxy-2,3-naphthalenedicarboxylate (32 g, 89 mmol) was added to a solution of sodium hydroxide (20 g) in ethanol (200 ml) and water (40 ml) and stirred for 1.5 h at 60° C. The reaction was cooled and the thick white suspension was filtered. The solid was dissolved in a mixture of ethyl acetate (200 ml) and water (800 ml). The layers were separated and the aqueous was acidified with hydrochloric acid (2M, 120 ml). The aqueous was extracted with ethyl acetate (2x) and the combined organics were dried (MgSO$_4$). Evaporation of the solvent under vacuum gave 1,4-diethoxy-2,3-naphthalenedicarboxylic acid as a white solid (25 g, 92%).

$\delta$H [$^2$H$_6$]-DMSO 13.26, (2H, s), 8.15, (2H, m), 7.72, (2H, m), 4.13, (4H, q), 1.42 (6H, t).

Intermediate 4
1,4-Diethoxy-2,3-naphthalenedicarboxylic anhydride

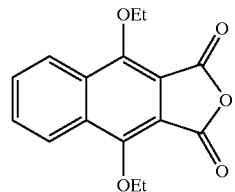

1,4-Diethoxy-2,3-naphthalenedicarboxylic acid (25 g, 82 mmol) was added to a solution of thionyl chloride (23.3 g) in chloroform (150 ml) and stirred at reflux for 1 h. The resulting solution was cooled and evaporated to dryness. Further chloroform was added and evaporation repeated to give 1,4-diethoxy-2,3-naphthalenedicarboxylic anhydride as a yellow solid (23.3 g, 99%).

$\delta$H [$^2$H$_6$]-DMSO 8.42, (2H, m), 7.93, (2H, m), 4.53, (4H, q), 1.46, (6H, t).

Intermediate 5
Ethyl[4(4,9-diethoxy-1,3-dioxo-1,3-dihydro-2H-benzo[f]isoindol-2-yl)phenyl]acetate

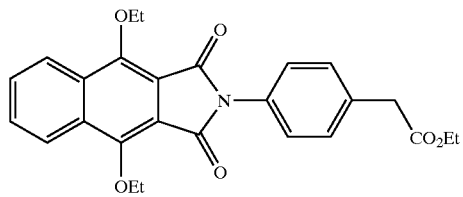

1,4-Diethoxy-2,3-naphthalenedicarboxylic anhydride (23.3 g, 81.5 mmol) and ethyl (4-aminophenyl)acetate (14.8 g, 82 mmol) were refluxed under nitrogen in acetic acid (160 ml) overnight. The mixture was cooled to room temperature and poured into water (1 L). The white solid was filtered, washed with water and dissolved in dichloromethane (800 ml). The solution was washed with water, brine and dried (MgSO$_4$) and the solvent evaporated under vacuum to give ethyl [4-(4,9-diethoxy-1,3-dioxo-1,3-dihydro-2H-benzo[f]isoindol-2-yl)phenyl]acetate as an off-white solid (33 g, 96%).

$\delta$H [$^2$H$_6$]-DMSO 8.40, (2H, m), 7.87, (2H, m), 7.42, (4H, s), 4.47, (4H, q), 4.12, (2H, q), 3.75 (2H, s), 1.45, (6H, t), 1.21, (3H, t).

EXAMPLE 1

Step 1

Ethyl [4-(4,9-diethoxy-1-oxo-1,3-dihydro-2H-benzo[f]isoindol-2-yl)phenyl]acetate

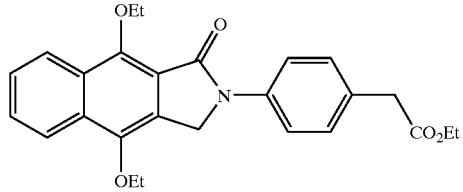

Ethyl [4-(4,9-diethoxy-1,3-dioxo-1,3-dihydro-2H-benzo[f]isoindol-2-yl)phenyl]acetate (339, 73 mmol) and zinc (909, 1.38 mol) were refluxed in acetic acid for 66 h. An additional quantity of zinc (25 g, 0.38 mol) was added and reflux continued for 18 h. The mixture was filtered hot and the filtrate was evaporated to a yellow solid. The solid was purified by 800 g Biotage column eluting with 20% ethyl acetate/hexane to give a white solid, which was triturated in ether to give a white solid. A further fraction was obtained by crystallisation from the ether residues. A total of 10.2 g, 32% of ethyl [4-(4,9-diethoxy-1-oxo-1,3-dihydro-2H-benzo[f]isoindol-2-yl)phenyl]acetate was obtained.

$\delta$H CDCl$_3$ 8.42, (1H, d), 8.18, (1H, d), 7.88, (2H, d), 7.63, (2H, m), 7.38, (2H, d), 5.00, (2H, s), 4.51, (2H, q), 4.26, (2H, q), 4.18, (2H, q), 3.65, (2H, s), 1.57, (6H, m), 1.28, (3H, t).

EXAMPLE 1

Step 2
[4-(4,9-diethoxy-1-oxo-1,3-dihydro-2H-benzo[f]isoindol-2-yl)phenyl]acetic Acid

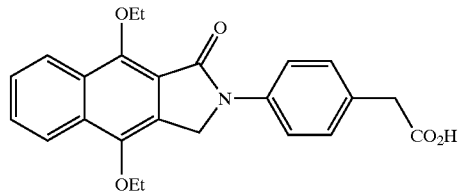

Ethyl [4-(4,9-diethoxy-1-oxo-1,3-dihydro-2H-benzo[f]isoindol-2-yl)phenyl]acetate (5.86 g, 13.5 mmol) and potassium carbonate (12 g) were added to a mixture of ethanol (146 ml) and water (70 ml) and heated to reflux for 2 h. The solution was cooled to room temperature and the solvent evaporated under vacuum to leave an off-white solid. The solid was slurried in water and the water was evaporated under vacuum. The residue was stirred in hydrochloric acid (2N) for 2 h, filtered and washed with water. Drying of the solid at 40° C. in a vacuum oven gave [4-(4,9-diethoxy-1-oxo-1,3-dihydro-2H-benzo[f]isoindol-2-yl)phenyl]acetic acid as a white solid (4.5 g, 82%)

$\delta$H [$^2$H$_6$]-DMSO 12.27, (1H, b), 8.25, (1H, d), 8.12, (1H, d), 7.86, (2H, d), 7.61, (2H, m), 7.27, (2H, d), 5.10, (2H, s), 4.34, (2H, q), 4.25, (2H, q), 3.54, (2H, s), 1.41, (3H, t), 1.37, (3H, t). MS 406, [MH$^+$]

What is claimed is:

1. [4(4,9-diethoxy-1-oxo-1,3-dihydro-2H-benzo[f]isoindol-2-yl)phenyl]acetic acid.

2. A composition comprising the compound according to claim 1 in admixture with one or more physiologically acceptable carriers or excipients.

3. The composition according to claim 2, further comprising one or more therapeutic agents selected from the group consisting of a cyclooxygenase 2 inhibitor, a 5-lipoxygenase inhibitor, low dose aspirin, non-steroidal anti-inflammatory drugs, a leukotriene receptor antagonist, disease modifying anti-rheumatic drugs, an adenosine 1 agonist, a recombinant human tumor necrosis factor receptor fusion protein, a sodium channel antagonist, an N-methyl D-aspartate antagonist, and a 5HT1 agonist.

4. A method of treating neuropathic pain in a mammal in need thereof comprising administering an effective amount of the compound according to claim 1.

5. A method of treating colon cancer in a mammal in need thereof comprising administering an effective amount of the compound according to claim 1.

6. A method of treating migraine in a mammal in need thereof comprising administering an effective amount of the compound according to claim 1.

7. A method for increasing the latency of HIV infection in a mammal in need thereof comprising administering an effective amount of the compound according to claim 1.

8. A process for preparing the compound according to claim 1, comprising the step of reducing the compound

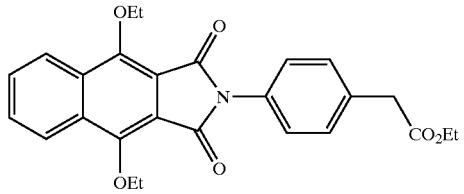

with a suitable reducing agent, followed by separation of Isomers and deprotection.

* * * * *

UNITED STATES PATENT AND TRADEMARK OFFICE
CERTIFICATE OF CORRECTION

PATENT NO. : 6,861,441 B1
DATED : March 1, 2005
INVENTOR(S) : Nicholas Maughan Clayton et al.

It is certified that error appears in the above-identified patent and that said Letters Patent is hereby corrected as shown below:

Title page,
Item [56], References Cited, insert the following:
-- FOREIGN PATENT DOCUMENTS
WO 99/47497
WO 00/18405
WO 00/20371
WO 00/20398

OTHER PUBLICATIONS,
Dumais, N., et al., "Prostaglandin E2 Up-Regulates HIV-1 Long Terminal Repeat-Driven Gene Activity in T Cells Via NF-kB-dependent and -independent Signaling Pathways" J. Biol. Chem., vol. 273, No. 42 pp. 27306-27314.

Rufer, C., et al. "New acylated 2-(4-aminophenyl)-propionicacids as anti-inflammatory agents" Eur J. Med. Chem-chim. Ther. 13(2)(1978) pp. 193-198 --.

Signed and Sealed this

Twelfth Day of July, 2005

JON W. DUDAS
*Director of the United States Patent and Trademark Office*